(12) United States Patent
Lazarus

(10) Patent No.: US 6,641,266 B1
(45) Date of Patent: Nov. 4, 2003

(54) CLIP-ON GUARD

(75) Inventor: Mark James Lazarus, Brentwood (GB)

(73) Assignee: Innovations for Trade and Technology, Essex (GB)

( * ) Notice: Subject to any disclaimer, the term of this patent is extended or adjusted under 35 U.S.C. 154(b) by 0 days.

(21) Appl. No.: 10/210,463

(22) Filed: Jul. 31, 2002

(51) Int. Cl.$^7$ .................................................. G02C 3/00
(52) U.S. Cl. ............................................. 351/155; 2/10
(58) Field of Search ...................... 381/155, 41, 158; 2/10, 12, 15, 13

(56) References Cited

U.S. PATENT DOCUMENTS 1,228,341 A * 5/1917 Maynard .......................... 2/10
1,829,538 A   10/1931 Prichard
2,717,385 A    9/1955 Linster

FOREIGN PATENT DOCUMENTS

CH    585529    3/1977
FR    7307366   9/1974

* cited by examiner

Primary Examiner—Hung Xuan Dang
(74) Attorney, Agent, or Firm—Wood, Phillips, Katz, Clark & Mortimer

(57) ABSTRACT

A guard for headgear, the guard comprising a transparent guard member 1 and releasable attachment means in the form of a spring clip 3 to attach the guard to extend downwardly from the headgear, wherein the guard member 1 is pivotable about an edge, such as a peak, of the headgear.

12 Claims, 4 Drawing Sheets

CLIP-ON GUARD

The present invention relates to a clip-on guard, and in particular to a clip-on guard for deflecting rain from a pair of spectacles during sporting events. The majority of spectacle wearers find difficulty in keeping rain off the lenses of their spectacles, particularly when involved in an outdoor sporting activity. This decreases their performance, as they are unable constantly to maintain a clear line vision without the need to wipe the surface of their lenses occasionally. This is a problem in many outdoor sporting activities, such as golf, fishing, cycling, shooting, sailing and outdoor bowling, and is a particular problem when such sports are taken up professionally.

The present invention seeks to alleviate the aforementioned problem by providing a side guard which can be attached to headgear in order to deflect rain from the spectacle wearer's lenses to prevent drops from forming on the lens surfaces.

The term headgear, for the purposes of this application, refers to hats, caps and visors and excludes spectacles.

Accordingly, there is provided headgear having a guard extending downwards therefrom, the guard comprising a transparent guard member and releasable attachment means to attach the guard to the headgear, wherein the guard member is pivotable about an edge of the headgear.

In a preferred embodiment, the headgear further comprises at least one further guard member releasably attached to the headgear.

Preferably, the or each guard is clippable onto the rim of the headgear.

Advantageously, the or each guard can be adapted to be clipped onto any shape of hat, peaked cap or visor, and may be formed to conform with the shape of the hat, cap or visor to which it is intended to be clipped.

The or each guard member is preferably made of polycarbonate or other clear plastic, but can also be made of tinted plastic or glass.

Alternatively, the or each guard member may be formed from polarised polycarbonate so to deflect sunlight from the spectacle lenses.

An embodiment will now be described, by way of example, with reference to the accompanying Figures in which.

Figure 1:
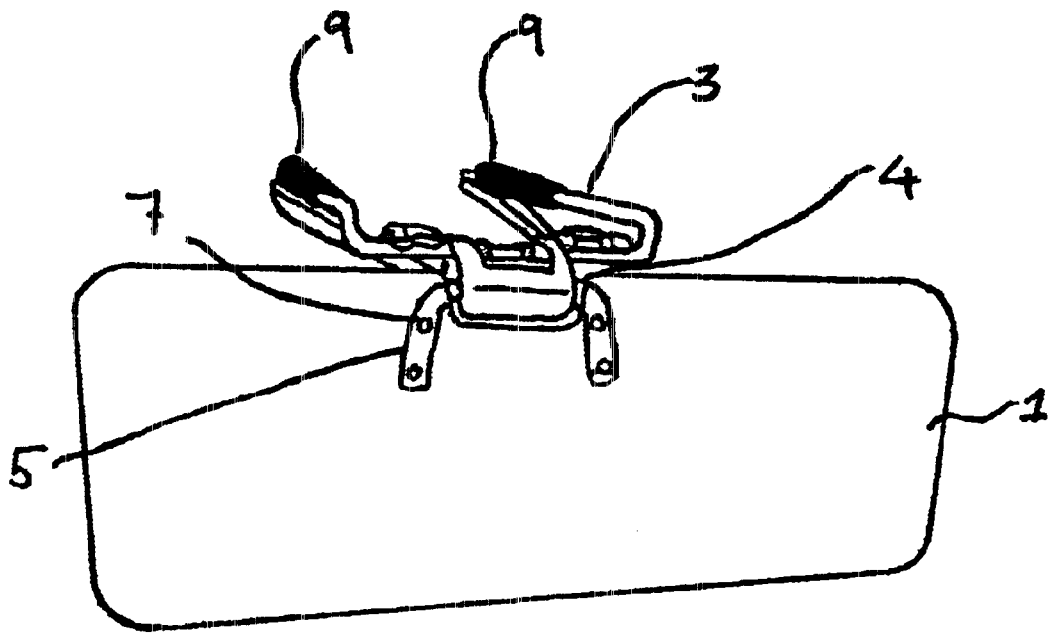
FIG. 1 is a perspective view of a clip-on guard constructed in accordance with the present invention.

Referring to FIG. 1, the clip-on guard comprises a transparent plastics guard member 1 having a resilient spring clip 3 pivotably attached thereto. Although FIG. 1 shows the guard member 1 as being substantially rectangular in shape, it will be apparent that the guard member could be formed in any shape, like, for example, that shown in FIG. 4. Indeed, it is preferable that the guard member 1 is formed in a shape that corresponds to the shape of the headgear to which it is intended to be attached.

The guard member 1 has a indentation 4 in one of its edges. An upturned U-shaped member 5 is attached to the guard member 1 by a plurality of rivets 7. The base of the U-shaped member 5 extends across the indentation 4 in the guard member 1, and is received by the spring clip 3.

Figure 2:
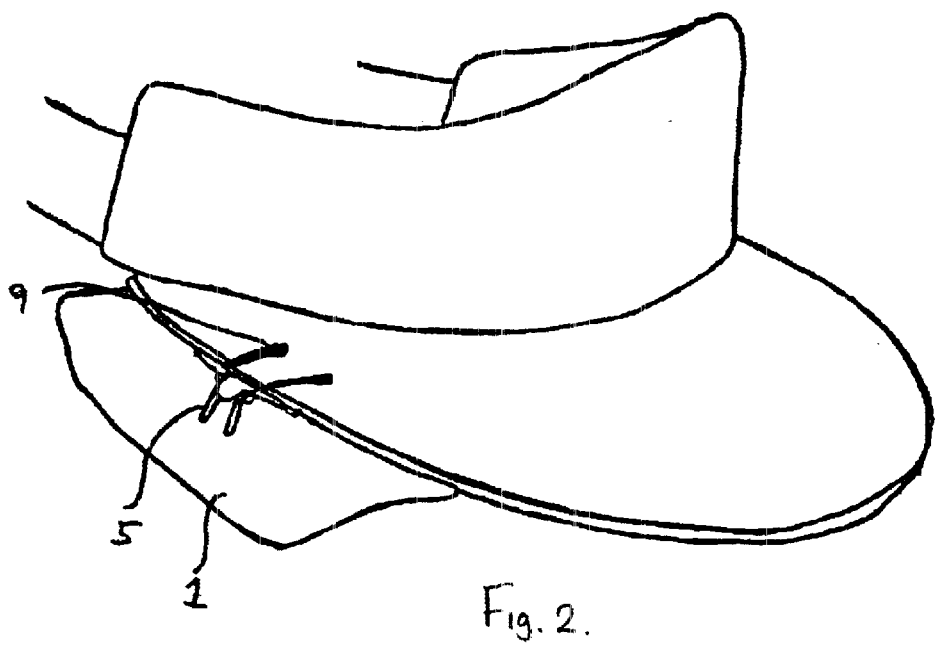
FIG. 2 illustrates the clip-on guard of FIG. 1, in use, attached to a visor.
Figure 3:
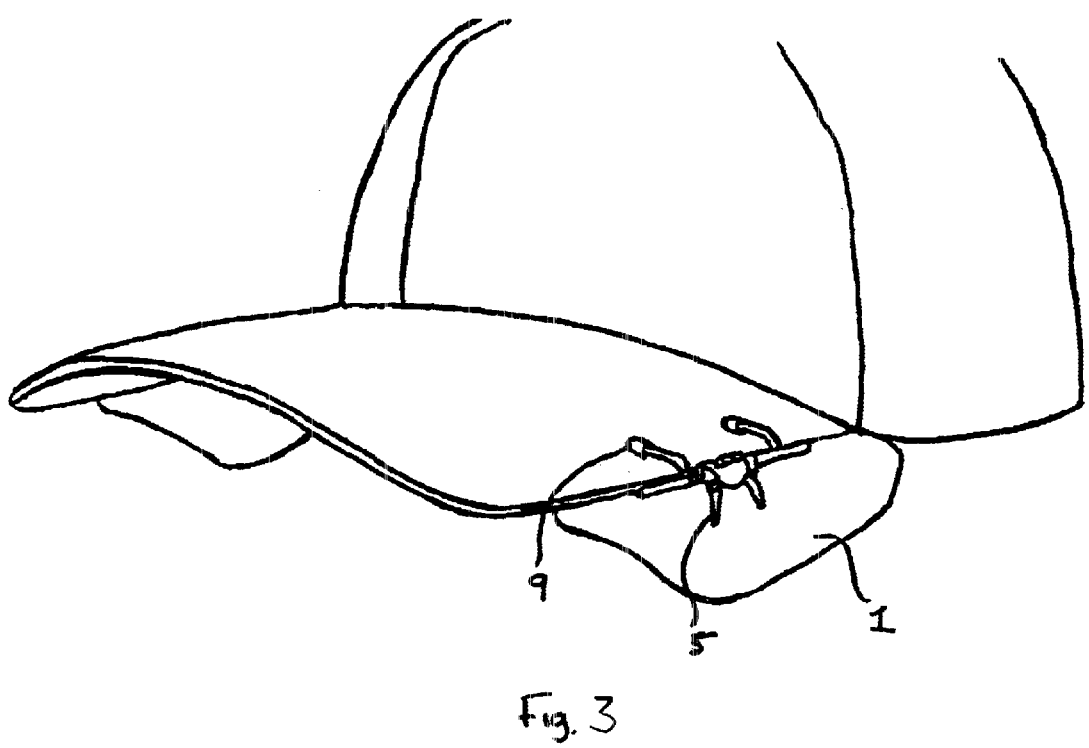
FIG. 3 illustrates the clip-on guard, in use, attached to a peaked cap.

In use, the clip-on guard is attached to the headgear by placing a rim of the headgear in between pairs of arms 9 of the spring clip 3, the arms being biased together so as to clip the clip-on guard firmly in place. This is clearly shown in FIGS. 2 and 3.

Figure 4:
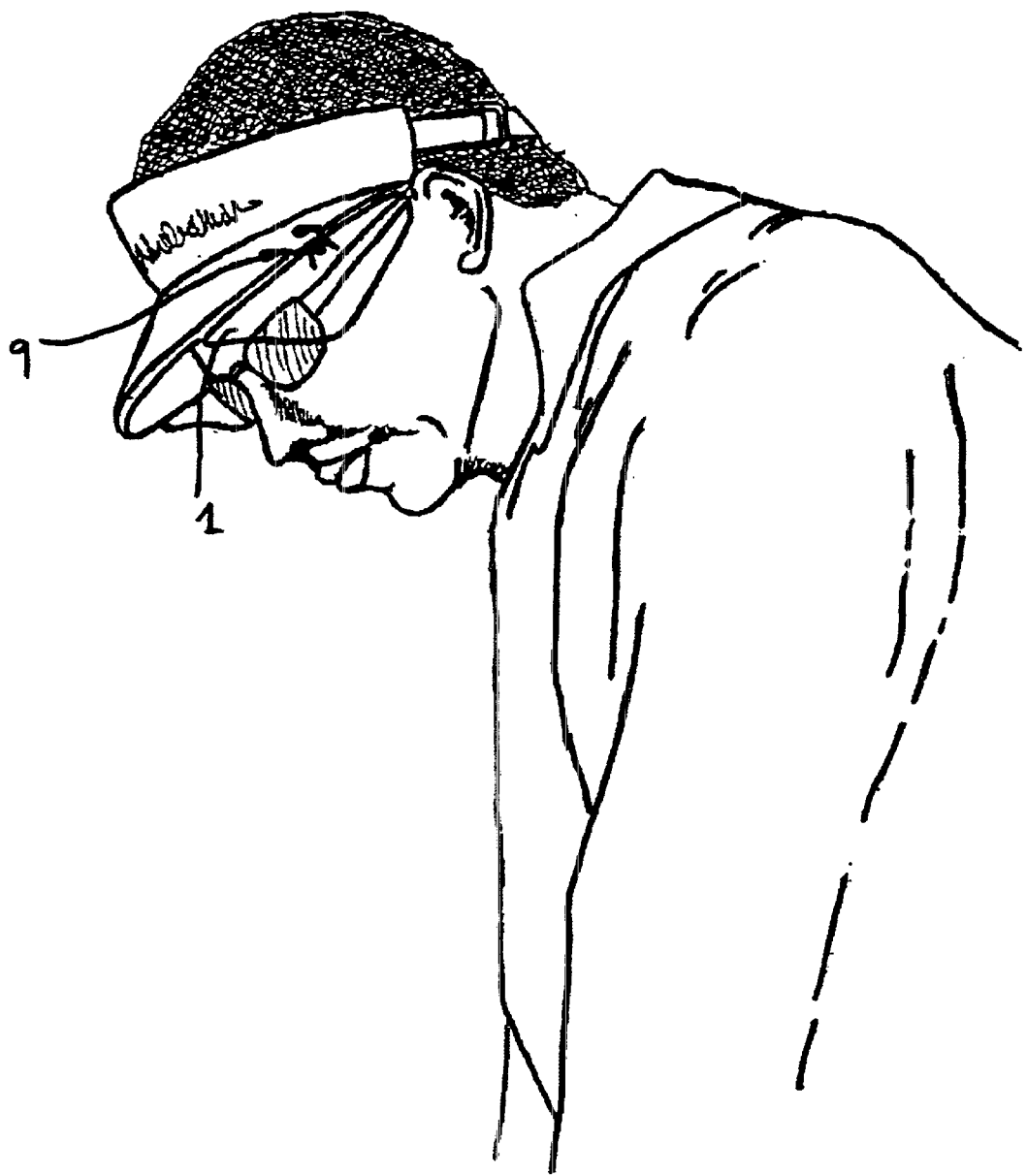
FIG. 4 illustrates the clip-on guard attached to visor, used for example, for golf.

In use, the guard member 1 extends downwards from the headgear, and acts as a barrier to rain so as to deflect the rain away from the eyes of the user, or the lenses of the users spectacles if he or she is a spectacle wearer (see FIG. 4).

Furthermore, the guard member 1 may deflect sunlight from the eyes of the user, if the guards members are made from a suitable polarised plastics material.

Figure 5:
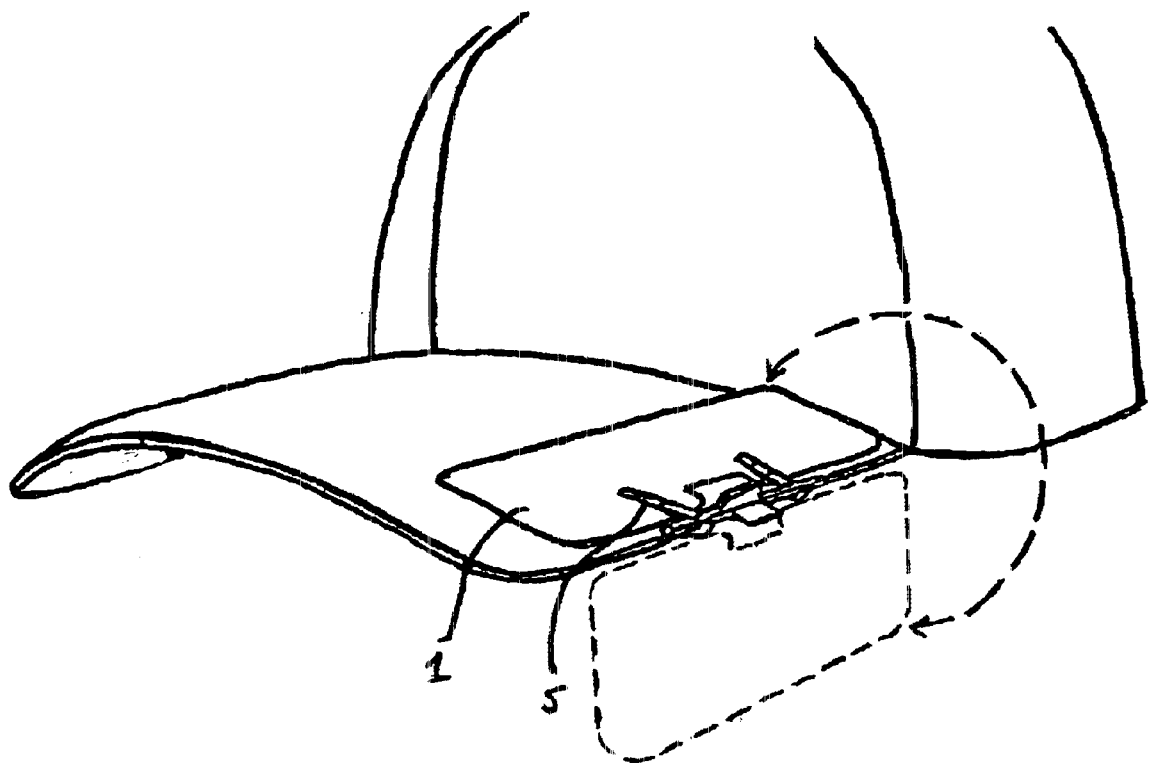
FIG. 5 shows how the clip-on guard is pivotably attached to a peaked cap.

Referring to FIG. 5, the guard member 1 is attached to the spring clip 3 in such a way as to be pivotable about the U-shaped member 5 of the guard member. This allows the guard member 1 to pivot, in use, with respect to the rim of the headgear. Consequently, in the event that rain or sunlight are not causing as problem, the guard can be flipped onto the top-side of a peaked cap as can be seen in FIG. 5.

Although the embodiment hereinbefore described refers to the guard member being made of plastics material, it is clearly the case that other transparent materials can be used such as glass, and the material can be clear, tinted or polarised.

Furthermore, the although the embodiment described only refers to one guard member, it will be apparent that at least one further guard member may be used on the same headgear to deflect rain or sunlight from any angle.

What is claimed is:

1. A guard for headgear, the guard comprising a transparent guard member having a releasable clip to attach the guard to the headgear such that the guard member extends downwardly therefrom, wherein the guard member is pivotable about an edge of the headgear and wherein the guard member extends substantially along part of a rim of the headgear, the edge of the guard member being shaped so as to conform to the shape of that part of the rim such that little or no gap exists between the rim and the edge of the guard member.

2. A guard according to claim 1, further comprising at least one further guard member releasably attached to the headgear.

3. A guard according to claim 1, wherein the releasable attachment means of the guard comprises a spring clip.

4. A guard according to claim 3, wherein the guard member is clipped to a rim of the headgear.

5. A guard according to claim 4, wherein the guard member is made from a plastics material.

6. A guard according to claim 4, wherein the guard member is made from glass.

7. A guard according to claim 1, wherein the guard member has a clear surface.

8. A guard according to claim 1, wherein the guard member has a tinted surface.

9. A guard according to claim 1, wherein the guard member has a polarised surface.

10. A guard according to claim 1, wherein the guard member is shaped so as to correspond with the shape of the headgear.

11. Headgear incorporating a guard as claimed in claim 1.

12. A guard according to claim 1, wherein said guard member is pivotable about the rim of the headgear between a first position extending downwardly from the rim and a second position on the top side of the headgear.

* * * * *